(12) United States Patent
Franz et al.

(10) Patent No.: US 12,424,311 B2
(45) Date of Patent: Sep. 23, 2025

(54) EVALUATION UNIT FOR A MEDICAL SYSTEM

(71) Applicant: Drägerwerk AG & Co. KGaA, Lübeck (DE)

(72) Inventors: Frank Franz, Lübeck (DE); Simon Gisch, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 569 days.

(21) Appl. No.: 17/879,876

(22) Filed: Aug. 3, 2022

(65) Prior Publication Data

US 2023/0042311 A1 Feb. 9, 2023

(30) Foreign Application Priority Data

Aug. 6, 2021 (DE) ...................... 10 2021 120 512.3

(51) Int. Cl.
*G16H 40/40* (2018.01)
*G06F 11/07* (2006.01)
*G16H 40/63* (2018.01)

(52) U.S. Cl.
CPC ......... *G16H 40/40* (2018.01); *G06F 11/0736* (2013.01); *G06F 11/0772* (2013.01); *G16H 40/63* (2018.01)

(58) Field of Classification Search
CPC ........ G16H 40/40; G16H 40/63; G16H 20/00; G16H 50/30; G06F 11/0736; G06F 11/0772

USPC ........................................................ 705/2–3
See application file for complete search history.

(56) References Cited

U.S. PATENT DOCUMENTS

| | | | | |
|---|---|---|---|---|
| 10,872,694 | B2 * | 12/2020 | Maeta | G16H 40/63 |
| 2020/0383647 | A1 * | 12/2020 | Freeman | A61B 5/7264 |
| 2021/0145300 | A1 * | 5/2021 | Indorf | G16H 40/63 |
| 2021/0287803 | A1 * | 9/2021 | Radrich | A61B 5/0004 |

FOREIGN PATENT DOCUMENTS

| | | | | |
|---|---|---|---|---|
| JP | | 6719799 B1 | 7/2020 | |
| WO | WO-2010046820 A1 * | | 4/2010 | A61B 5/0002 |

* cited by examiner

*Primary Examiner* — Joy Chng
(74) *Attorney, Agent, or Firm* — McGlew and Tuttle, P.C.

(57) ABSTRACT

An evaluation unit (100) classifies a current treatment situation for a signal connected medical system. A receiving module (110) receives a plurality of treatment signals (112) that indicates a value (116) for a patient parameter (115) and a signal quality. A processing module stores values of patient parameters received at past times with a respective time stamp (125) indicating the time and a quality index (127) assigned to the respective value or group of values and detects a presence of a trigger signal (124) and calculates an evaluation score (134) using a stored calculation rule (132). The calculation uses the stored values of patient parameters as a function of the respective time stamp. The processing module calculates a quality indicator (138) using a stored quality metric (136) depending on the associated quality indices of the values of patient parameters necessary for the calculation of the evaluation score.

20 Claims, 4 Drawing Sheets

EVALUATION UNIT FOR A MEDICAL SYSTEM

CROSS REFERENCE TO RELATED APPLICATIONS

This application claims the benefit of priority under 35 U.S.C. § 119 of German Application 10 2021 120 512.3, filed Aug. 6, 2021, the entire contents of which are incorporated herein by reference.

TECHNICAL FIELD

The invention relates to an evaluation unit for a signal connected medical system for classifying a current treatment situation. Furthermore, the invention relates to a medical system with an evaluation unit according to the invention and a process for classifying a current treatment situation.

TECHNICAL BACKGROUND

It is known that for a clinical evaluation in a medical setting, a score can be given that is determined based on a variety of different diagnostic parameters. Such diagnostic parameters may include, for example, age, pre-existing conditions, kidney function, lung function, other laboratory values, and the like. Such an assessment allows a patient's condition to be classified on a typically one-dimensional scale. This allows the attending physician to quickly get a rough picture of the patient's condition. Determining the appropriate score is based on well-known formulas, such as those that have become commonly used for severity classification during patient admission (Simplified Acute Physiology Score, SAPS), monitoring organ function (Sepsis-related Organ Failure Assessment, SOFA), and measuring therapeutic effort (Therapeutic Intervention Scoring System, TISS).

The automated provision of such point values within networked medical systems is also known, whereby a respective medical device outputs corresponding data for determining the point value to a corresponding evaluation unit.

SUMMARY

It is an object of the present invention to provide an improved evaluation unit, in particular an evaluation unit for calculating a particularly reliable evaluation score (evaluation index).

According to a first aspect of the invention, an evaluation unit for a signal-connected medical system for classifying a current treatment situation is provided for solving this task, comprising a receiving module, a processing module, and an output module.

The receiving module is configured to receive a plurality of treatment signals, wherein a respective treatment signal indicates a value for a patient parameter and a signal quality.

The processing module has an internal memory in which values of patient parameters received at past times are stored with a respective time stamp indicating this past time (indicating a receipt time) and a quality index assigned to the respective value or a group of values, wherein for at least one value or a group of values the quality index is based on the signal quality present at the time of reception. Furthermore, the processing module is configured to detect the presence of a trigger signal and, after the detection of the trigger signal, to calculate an evaluation score using a stored calculation rule, the calculation being performed using the stored values of patient parameters as a function of the respective time stamp, and an absence of a value of a patient parameter which is necessary for the calculation of the evaluation score and/or of a current value for this patient parameter in view of the respective time stamp being indicated by the evaluation unit. Furthermore, the processing module is configured to calculate at least one quality indicator on the basis of a stored quality metric depending on the assigned quality indices of the values of patient parameters necessary for the calculation of the evaluation score.

The output module is configured to provide an output signal, wherein the output signal indicates at least the evaluation score and the quality indicator.

Within the scope of the invention, it was recognized that automated processing of measured values can be carried out particularly reliably if, in addition to the values for the corresponding patient parameters, the signal quality of the signals corresponding thereto is also taken into account. To take into account the course of patient parameters and/or corresponding signal qualities, the respective time stamp is also provided.

Thus, a particularly reliable evaluation score can be provided according to the invention by having the quality indicator indicate the present level of reliability. This combines the known concept of determining an evaluation score for patient condition and the known concept of determining a quality indicator for a signal quality to enable a measure of the trustworthiness of the evaluation score provided.

Furthermore, the evaluation unit according to the invention advantageously indicates if patient parameters necessary for the calculation of the evaluation score are missing and/or outdated. Here, different time threshold values for different patient parameters can be predefined. Such a time threshold value indicates from which age of a value this value can no longer be used for the determination of the evaluation score. For example, the age of a patient is not subject to variance and therefore remains essentially unchanged, so that age as a patient parameter cannot become outdated, whereas, for example, respiratory rate can change rapidly to a large extent, so that such a patient parameter quickly becomes outdated, i.e., too old for a meaningful determination of the evaluation score. The quality index of a value may depend on the time threshold assigned to the corresponding patient parameter.

The timestamp is preferably a string that at least indirectly indicates a measurement time for the received value for the patient parameter. For example, the time stamp can indicate a time of output of the corresponding treatment signal.

The quality metric may be based on an accounting of received quality indices and/or at least in part on an accounting of the time course of values for patient parameters.

The evaluation unit according to the invention can advantageously be integrated into existing medical systems, whereby an appropriate communication link must be provided with components of the medical system for exchanging the plurality of treatment signals.

The individual modules of the evaluation unit according to the invention can be arranged in a common housing or at least partially spaced apart. Particularly preferably, the modules are executed by a common processor, whereby they are separated from each other at least at the software level.

The respective treatment signal can provide the signal quality directly in the form of a quality index indicating the signal quality and/or indicate the signal quality indirectly via the value of the patient parameter and/or other signal components. For example, the value of the patient parameter may have a certain variance compared to other values of the patient parameter, allowing conclusions to be drawn about the signal quality in a known manner.

The evaluation unit according to the invention is particularly advantageous in view of manufacturer-specific data interfaces common in the acute medical field. Due to this partial lack of compatibility and/or comparability of output signals, evaluation indicators currently often have to be determined at least partially manually, by partially manually aggregating values from different devices. According to the invention, therefore, an evaluation unit is provided that can be independent of further devices of the medical system and with which the corresponding devices preferably exchange the plurality of treatment signals via a common communication standard. Such a communication standard can be, for example, the well-known standard IEEE 11073 SDC (Service-oriented Device Connectivity).

The evaluation unit according to the invention enables an automated and continuous determination of evaluation scores. In particular, the age of values received in the past for the patient parameters is taken into account during processing, so that a course of received data can be advantageously evaluated. Basically, the evaluation score according to the invention is a number or a value that indicates a classification of a currently present treatment situation in order to be able to indicate a current condition of the patient to the treating medical staff as quickly as possible.

According to the invention, the at least one quality indicator is a measure of the quality of the specific evaluation score. This is ensured by the fact that it results from the quality indices of the values of patient parameters relevant for the evaluation score.

The time stamp can be assigned to the respective value of the patient parameter by the receiving module and/or the processing module. A content of the time stamp may already have been included in the corresponding treatment signal or alternatively be assigned to the value of the patient parameter by the corresponding component of the evaluation unit, preferably after receipt of the corresponding treatment signal.

Preferred embodiments of the evaluation unit according to the invention are described below.

In a preferred embodiment, the processing module is configured to determine a respective quantitative influence of the patient parameters used on the calculated evaluation score and/or on the calculated quality indicator, and wherein the output module is further configured to indicate the determined quantitative influence of at least one patient parameter used, in particular to indicate it via the output signal. By indicating the quantitative influence of the respective patient parameter on the calculated evaluation score, it can be quickly and reliably grasped by the user of the evaluation unit which patient parameter currently has the greatest influence on the evaluation score. This makes it possible, for example, to quickly understand why certain steps in the patient's treatment have little or a particularly strong impact on the evaluation score. In addition, it can be used to assess whether the currently used evaluation score is suitable for evaluating a current patient condition of the treated patient. For example, if a patient parameter that did not change at all during treatment has a particularly large impact on the evaluation metric, this evaluation metric is probably not suitable for evaluating the current treatment. Preferably, the evaluation unit has a user interface via which an evaluation score to be used with a corresponding stored calculation rule to be used can be selected by the user of the evaluation unit, in particular can be selected from a predetermined group of evaluation scores.

In a particularly advantageous variant of the preceding embodiment, the processing module is configured to determine the quantitative influence using a sensitivity analysis or an error propagation analysis. Such analyses are known to those skilled in the art and are therefore not explained in detail below. By means of such an analysis it can be determined to what extent a certain variance of an influence quantity to be accounted for leads to a variance of the obtained result quantity. Such analyses are therefore particularly suitable for determining the quantitative influence of the corresponding patient parameter on the calculated evaluation score.

In an advantageous embodiment, the evaluation unit is configured to receive the trigger signal via the Receiving module, via a user interface, via a network interface and/or via a device interface. Such interfaces are known to the skilled person and are therefore not explained in detail below. Here, the interfaces can support cable-based communication and/or wireless communication. The trigger signal is thereby a signal that can be triggered in response to a received input signal, a received user interaction or the like. The trigger signal may be present here as a separate signal for the evaluation unit, or alternatively may be a signal within the medical system that simultaneously represents the trigger signal for the evaluation unit. Alternatively or additionally, the trigger signal is provided in a time-controlled manner. For example, the calculation of the evaluation score and the quality indicator can be triggered after regularly recurring time intervals, for example hourly, so that a corresponding time signal can simultaneously be a trigger signal.

In a further advantageous embodiment, the quality indicator is dependent on the timestamp of a value of a patient parameter necessary for the calculation of the evaluation score. In this embodiment, it is advantageously taken into account that an older value for the corresponding patient parameter is usually less reliable than a currently received value for this patient parameter. Thus, by taking the time stamp into account, an older value can be marked as less reliable than a current value. The number of time thresholds used here for the determination of the quality indicator depending on this can be dependent on the corresponding patient parameter, since there are patient parameters that vary very little over time, such as the patient's age, and patient parameters that vary very much over time, such as the patient's blood pressure. The time stamp can be taken into account, for example, in such a way that the quality index has a component, such as an additive component, that depends, in particular linearly depends, on the time interval between the receipt of the corresponding value for the patient parameter and the current time.

In another embodiment, the absence of a patient parameter necessary for calculating the evaluation score and/or a current value for that patient parameter given the respective timestamp is indicated by the evaluation unit outputting a request signal to the connected medical system. In this embodiment, the medical system can automatically output the missing value for the patient parameter and/or the current value for this patient parameter in response to the request signal. This particularly advantageously ensures automated provision of the evaluation score according to the invention with the at least one quality indicator.

In a particularly preferred embodiment, the evaluation unit is configured to receive static patient parameters and dynamic patient parameters. In this case, the processing module is configured to evaluate only time stamps for values of dynamic patient parameters for the calculation of the evaluation score, whereas values for static patient parameters are evaluated without taking the time stamp into account. In this embodiment, it is particularly advantageous to distinguish between patient parameters that hardly change, i.e., static, and patient parameters that change strongly, i.e., dynamic. Such an automated differentiation enables a particularly fast and simple classification of the patient parameters without having to store separate time stamps, time thresholds or the like.

Preferably, the evaluation unit is configured to receive the static patient parameters age, gender, weight and/or height of a patient. These patient parameters typically change little or at least very slowly during the treatment of the patient. Therefore, these static patient parameters are preferably processed differently by the evaluation unit according to the invention than rapidly changing patient parameters, such as blood pressure, heart rate, respiratory volume or the like, for which current values must be constantly available in order to provide a reliable evaluation metric for assessing the current condition of the patient.

In a particularly preferred embodiment, the quality index is based on a time course of a patient parameter and a statistical evaluation of this course. If the time course of the patient parameter shows a large variance, this may indicate poor signal quality. The evaluation of the time course can be performed alternatively or in addition to the evaluation of a usual signal quality index, such as an evaluation of the present signal-to-noise ratio. This can be used to perform a plausibility check during operation of the evaluation unit, indicating whether the variance in the course of the patient parameter is largely correlated and/or related to the present signal quality.

In another particularly preferred embodiment, the quality index is based on a temporal course of signal qualities of treatment signals for a group of received values of a respective patient parameter. Based on the course of signal qualities, a connection problem during the transmission of the corresponding patient parameter and/or an expected future course can be concluded. For example, a consistently high signal quality over the last monitored time intervals can indicate that there is also a high probability of high signal quality in the near future, so that this patient parameter can be classified as particularly reliable. This can be implemented by summing up previous signal qualities as part of the application of the quality metric. Alternatively or complementarily, poor signal quality or slowly deteriorating signal quality may be inferred to indicate a connectivity problem in the transmission of the patient parameter and an expected future poor signal quality as a result. Preferably, in this embodiment, the evaluation unit is further configured to output a connection problem indicated thereby to a user of the evaluation unit via a corresponding output in the event of poor signal quality persisting over a predetermined time interval. This output preferably takes place via the output module.

In a further embodiment, the calculation of the evaluation score is further dependent on the respective quality index of the values of patient parameters used. For example, the calculation rule for the evaluation score may provide for a weighting of patient parameter-dependent components of the calculation rule that is dependent on the corresponding quality index. Such a calculation rule for the evaluation score advantageously enables the change of the quantitative influence of a correspondingly used patient parameter depending on the stored quality index, thus, for example, depending on the signal quality of the treatment signal via which the value of the patient parameter was received.

In a particularly preferred variant of the preceding embodiment, the processing module is further configured to consider only values for the calculation of the evaluation score whose quality index is within a predetermined index target range. In this embodiment, values for the patient parameter having an assigned quality index that is outside the index target range are not considered for the calculation of the evaluation score. This prevents patient parameters that are not sufficiently up to date and/or are likely to be incorrect due to connectivity issues between the evaluation unit and the corresponding medical device from influencing the evaluation score.

In a particularly advantageous embodiment, the output module is further configured to trigger, based on the determined respective quantitative influence of a patient parameter, an output indicative of a failure from a predetermined group of failures, the predetermined group comprising, at least in part: Connection failure with a device providing a patient parameter; Device failure of a device providing a patient parameter; New value required for patient parameter. In this embodiment, the quantitative influence of a patient parameter is particularly advantageously taken into account to check whether a low signal quality and/or a quality index indicating a low signal quality has a relevant influence on the evaluation score. If the quantitative influence is above a predetermined influence threshold, the incident from the predetermined group of incidents leads to the corresponding output. Here, for example, the presence of the specific fault can be concluded on the basis of a predetermined assignment rule based on the quality index and/or a temporal progression of quality indices.

In a further embodiment, the output module is further configured to trigger an alarm in the connected medical system based on the calculated evaluation score and the calculated quality indicator if a predetermined evaluation threshold is reached and the quality indicator is simultaneously in a quality target range. In this embodiment, the evaluation unit according to the invention is particularly advantageously used for controlling an alarm depending on the evaluation indicator in order to inform the user of the evaluation unit and the connected medical system about the presence of a critical evaluation indicator. The consideration of the quality indicator provided in this context ensures that an evaluation indicator which probably deviates strongly from the evaluation indicator actually present, for example due to connection problems, does not lead to an alerting by the evaluation unit.

Preferably, an evaluation score type (an evaluation index type) can be selected from a predetermined group of evaluation score types via a user interface. An evaluation score type thereby indicates the relevant patient parameters and the calculation rule to be used. Examples of evaluation score types, such as SAPS, SOFA and TISS, have already been mentioned. It is particularly preferred that the stored quality metric is assigned to the corresponding calculation rule.

According to a second aspect of the invention, a medical system comprising an evaluation unit according to at least one of the preceding embodiments is provided for solving the above problem. Furthermore, the medical system according to the invention comprises a number of medical devices connected to the evaluation unit, wherein the medical devices are adapted to output treatment signals to the evaluation unit.

The medical system according to the second aspect of the invention comprises the evaluation unit according to the first aspect of the invention and consequently all advantages of this evaluation unit. In particular, the medical system according to the invention allows continuous determination and monitoring of the calculated evaluation score and the calculated quality indicator.

Preferably, the medical devices of the medical system communicate using a common communication protocol so that no conversion between different communication protocols is required to use the evaluation unit.

In a preferred embodiment, an adjustment of at least one predetermined treatment parameter of a medical device out of the number of medical devices triggers the trigger signal for the evaluation unit. Such a trigger signal ensures that the effects of adjusting the treatment parameter are detected by the user of the medical system. Thus, the user can detect a change in the evaluation score directly with the adjustment of the treatment parameter and thereby decide particularly reliably whether the adjustment of the treatment parameter is likely to have the desired effect.

According to a third aspect of the invention, a process for classifying a current treatment situation is provided for solving the above task. The process according to the invention comprises the following steps:

Receiving a plurality of treatment signals, wherein a respective treatment signal indicates a value for a patient parameter and a signal quality;

Storing values of patient parameters received at past times with a respective time stamp indicating this past time and a quality index assigned to the respective value or a group of values, wherein for at least one value or a group of values the quality index is based on the signal quality present at the time of reception;

Detecting a presence of a trigger signal;

Calculating an evaluation score using a stored calculation rule, wherein the calculation is performed using the stored values of patient parameters depending on the respective time stamp, and wherein a lack of a value of a patient parameter necessary for calculating the evaluation score and/or a current value for this patient parameter in view of the respective time stamp is indicated;

Calculating at least one quality indicator based on a stored quality metric depending on the assigned quality indices of patient parameter values required to calculate the evaluation score;

Providing an output signal, wherein the output signal indicates the evaluation score and the quality indicator.

The process according to the invention is carried out by the evaluation unit according to the invention, so that the advantages explained for the evaluation unit are also present for the process. In particular, the process according to the invention enables a continuous and automated output of an evaluation score and the corresponding quality indicator of this evaluation score and thereby a particularly reliable and simple classification of the current condition of a patient to be treated.

Preferably, the process according to the invention is at least partially executed by a microprocessor. The execution is thereby controlled by a corresponding computer program.

Preferably, all steps of the process according to the invention are carried out sequentially, whereby the depositing of values is preferably carried out largely continuously and consequently this process step can be carried out in parallel with other process steps of the process.

The process steps of the process are preferably carried out by a single device. In an alternative embodiment, the process steps are carried out spatially spaced apart from one another.

The invention will now be explained in more detail with reference to advantageous examples of embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
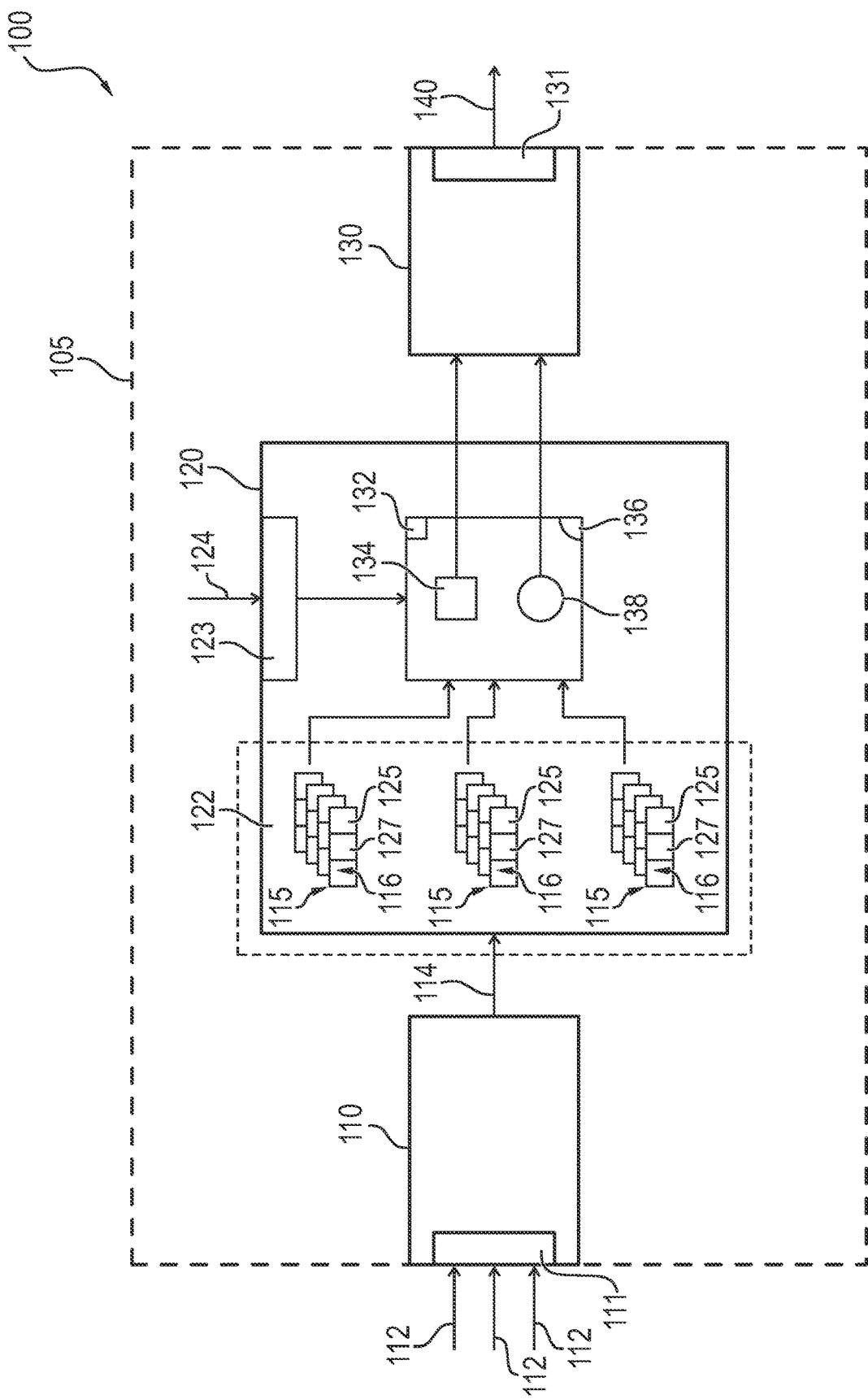
FIG. 1 is a schematic representation of a first embodiment of an evaluation unit according to a first aspect of the invention.

Referring to the drawings, FIG. 1 shows a schematic diagram of a first embodiment of an evaluation unit 100 according to a first aspect of the invention.

The evaluation unit 100 is configured to communicate with a signal-connected medical system for classifying a current treatment situation of a patient. For this purpose, the evaluation unit 100 has a receiving module 110, a processing module 120, and an output module 130.

The receiving module 110 is configured to receive a plurality of treatment signals 112, wherein a respective treatment signal 112 indicates a value 116 for a patient parameter 115 and a signal quality. In the illustrated embodiment, the receiving module 110 receives various treatment signals 112, with the signals enabling continuous reception of the patient parameters 115. The indicated signal quality is determined by an evaluation of the corresponding treatment signal 112 within the receiving module 110 and/or within the processing module 120. The receiving module 110 outputs the information received and pre-processed for further processing from the plurality of treatment signals 112 to the processing module 120 via a processing signal 114.

The processing module 120 has an internal memory 122 in which values 116 of patient parameters 115 received at past times are stored with a respective time stamp 125 indicating this past time (indicating a receipt time) and a quality index 127 assigned to the respective value 116 or a group of values. Thereby, for at least one value 116 or group of values, the quality index 127 is based on the signal quality present at the time of reception. The quality index 127 may be a constant value predetermined in a blanket manner for this type of patient parameter 115. Preferably, the quality index 127 is a value that decreases as the value 116, which is indexed by the timestamp 125, ages, thereby indicating a lower quality of the value 116. This can be mathematically implemented, for example, using a scaling with an exponential function that decreases exponentially with time. The quality index 127 may also be implemented via a statistical process, which is preferably implemented for a past plurality of values 116 for the corresponding patient parameter 115, to account for statistical variance in the measurement and/or transmission of those values 116.

The processing module 120 is further configured to detect a presence of a trigger signal 124. In the illustrated embodiment, detection of the trigger signal 124 is performed directly via a trigger receiving component 123. In other embodiments, reception of the trigger signal is performed, for example, via the receiving module 110 or via a separate module of the evaluation unit 100.

For example, a trigger for such a trigger signal may be a specific event, such as entering new patient data, starting a new treatment of a patient, and/or receiving a new value for a patient parameter. Alternatively or additionally, a trigger signal can trigger the classification by the evaluation unit 100, i.e. the determination of the evaluation score and the quality indicator, at regular time intervals. This is particularly advantageous in supporting automated operation of the evaluation unit.

After detection of the trigger signal 124, an evaluation score 134 is calculated using a stored calculation rule 132. In this case, the calculation is performed using the stored values 116 of patient parameters 115 depending on the respective time stamp 125. The age of the corresponding value 116 indicated by the time stamp 125 may explicitly be a component of the calculation rule 132. Alternatively or additionally, the age of the corresponding value 116 indexed by the timestamp 125 may be a criterion checked by the processing module 120 so as not to use the value for calculation within the calculation rule 132 if the age value is too large. Such a time threshold value is preferably not the same for all patient parameters 115, but is dependent on dynamics typically present for that patient parameter. For example, a patient's weight typically changes much more slowly than heart rate, so the corresponding stored value for such a parameter need not be as up to date to be considered within the scope of the calculation instruction 132. In this regard, a lack of a value of a patient parameter 115 necessary for the calculation of the evaluation score 134 and/or a value for that patient parameter that is current given the respective timestamp 125 is indicated by the evaluation unit. In the illustrated embodiment example, such indication is effected via the output module 130. A further indicating device, via which this indication is effected visually to the user of the evaluation unit 100, is not shown in FIG. 1.

Calculation rules for calculating an evaluation score are generally known in the medical environment. These are typically an assignment table or a mathematical formula that assigns a scalar evaluation score to corresponding values for the patient parameters. For example, well-known formulas are mentioned here, which have become common for severity classification during patient admission (Simplified Acute Physiology Score, SAPS), monitoring of organ function (Sepsis-related Organ Failure Assessment, SOFA) and measurement of therapy effort (Therapeutic Intervention Scoring System, TISS).

The processing module 120 is further configured to calculate at least one quality indicator 138 based on a stored quality metric 136 depending on the associated quality indices 127 of the values 116 of patient parameters 115 necessary for calculating the evaluation score 134. Various processes are possible for determining the quality according to the invention. For example, the quality indices 127 can be directly offset according to a mathematical rule to thereby obtain the quality indicator 138. Alternatively or additionally, in addition to the quality indices, further variables, such as an age of the corresponding value indexed on the basis of the time stamp 125, a predetermined weighting value assigned to the corresponding patient parameter, or the like, can be used to offset the quality indices 127. Alternatively or additionally, a subsequent result evaluation for the evaluation metric can be used manually or in a partially automated manner in order to find out, between different possible weightings for offsetting the quality indices, the weighting and consequently the quality metric that has led to the best subsequent result evaluation for the present condition and/or for the present patient parameter. Particularly preferably, the quality metric 136 comprises an error propagation analysis, wherein the individual quality indices 127 correspond to an error of the respective value 116 and, consequently, the quality indices 127 are offset against each other according to one of the known processes for error propagation analysis. Various types of error propagation analysis are known, such as determining a total error of the calculation rule according to the Gaussian error propagation law.

The output module 130 is configured to provide an output signal 140, wherein the output signal 140 indicates at least the evaluation score 134 and the quality indicator 138.

The output signal may indicate at least one quality index 127 of a patient parameter 115 and/or other information regarding at least one of the patient parameters 115, in addition to the evaluation score 134 and the quality indicator 138. Alternatively, or additionally, the output signal 140 may indicate a recommended action for the user of the evaluation unit 100 from a group of predetermined instructions. In this case, the recommended action results from a stored assignment that assigns a recommended action to a combination of the evaluation score and the quality indicator, as well as from the calculation rule used.

In the illustrated embodiment, the processing module 120 is connected to the output module 130 such that the evaluation score 134 and the quality indicator 138 are communicated to the output module 130 as separate data such that the output module 130 generates and exercises the output signal 140 accordingly.

In the illustrated embodiment, the Receiving module 110 comprises a Receiving interface 111 and the output module 130 comprises an output interface 131. Both interfaces 111, 131 are configured for wireless communication with further devices of the not illustrated surrounding medical system. In an embodiment not shown, the communication is cable-based. The configuration of such interfaces is known to the person skilled in the art and is therefore not explained in detail below.

The modules of the illustrated evaluation unit 100 are arranged in a common housing 105. Preferably, these modules are operated by a common microprocessor and are thereby separated from each other at least at the software level.

Figure 2:
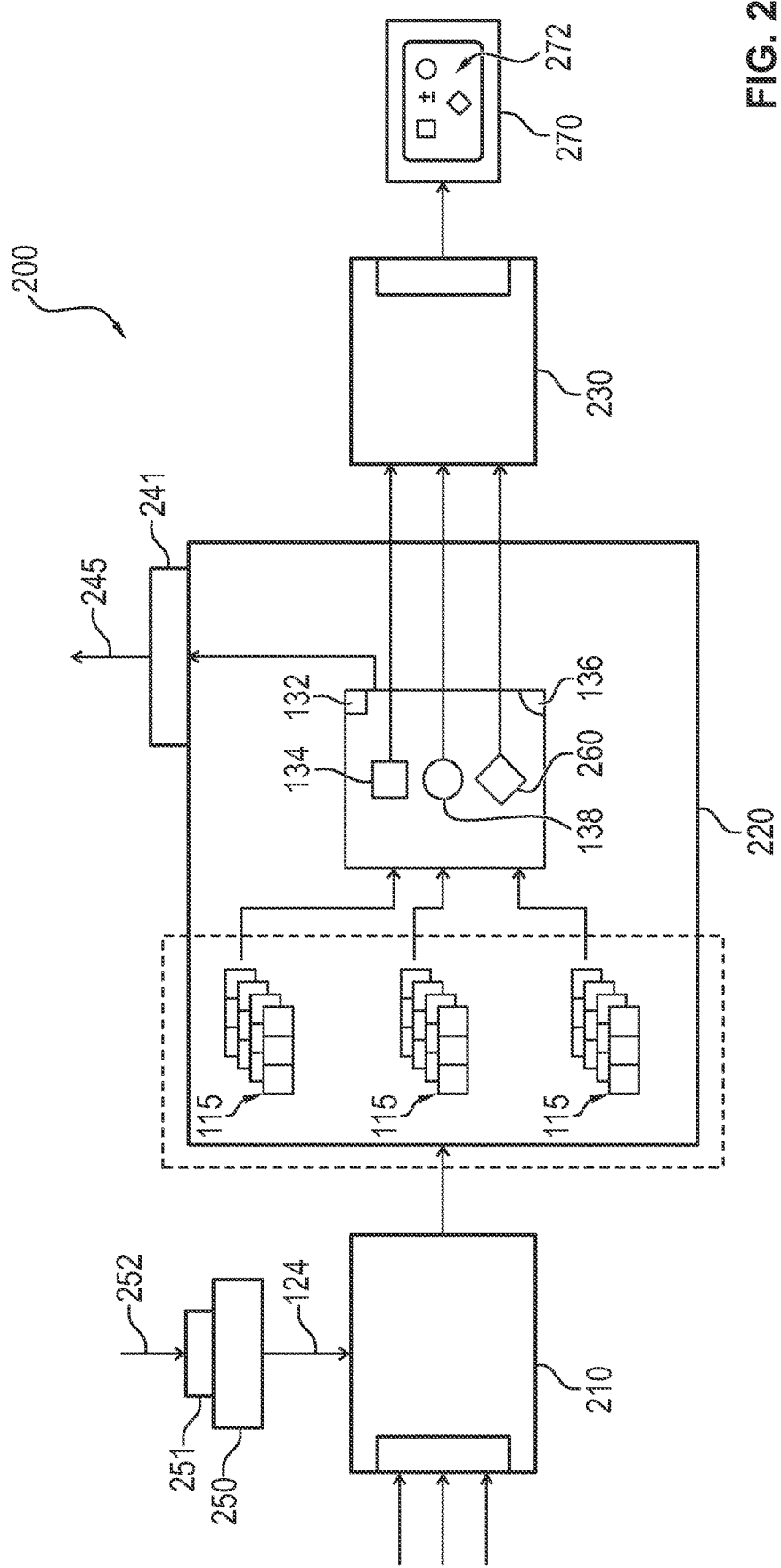
FIG. 2 is a schematic representation of a second embodiment of the evaluation unit according to the first aspect of the invention.

FIG. 2 shows a schematic view of a second embodiment of an evaluation unit 200 according to the first aspect of the invention.

The evaluation unit 200 differs from the evaluation unit 100 shown in FIG. 1 in that, among other things, the trigger signal 124 is triggered by a user input 252 to a separate user interface 251 of an input module 250 and then received by the Receiving module 210. Such triggering of the trigger signal 124 may be alternative or complementary to triggering via another interface of the evaluation unit.

Furthermore, the evaluation unit 200 differs in that the processing module 220 is also adapted to determine a respective quantitative influence 260 of the patient parameters used on the calculated evaluation score 134 and/or on the calculated quality indicator 138. Such a quantitative influence 260 is preferably determined based on a sensitivity analysis or based on an error propagation analysis. For this purpose, it can be investigated, for example, to what extent a small change in an input variable for the calculation rule 132 and/or the quality metric 136 leads to a change in the result, i.e. to a change in the calculated evaluation score 134 and/or to a change in the calculated quality indicator 138. Hereby, the influence of a respective input variable on the result can be identified. In particular, it can be determined which of the input variables, i.e. which of the patient parameters, has the strongest influence on the corresponding result.

Preferably, the output module 230 is further configured to indicate the determined quantitative influence 260 of at least one patient parameter 115 used, in particular via the output signal 140. As shown in FIG. 2, the output signal 140 causes a visual output 272 provided at an external output device 270 to include an output of the quantitative influence in addition to an output of the evaluation score and the quality indicator. The output of the quantitative influence 260 may include a listing of a plurality of influences of the corresponding patient parameters. For example, the three most influential patient parameters may be presented sorted by influence. Preferably, the influence is presented using a scalar value.

In addition, the evaluation unit 200 is adapted to trigger the absence of a value of a patient parameter necessary for calculating the evaluation score 134 and/or a current value for that patient parameter given the respective timestamp by outputting a request signal 245 to the connected medical system via a corresponding request interface 241.

In the following, a listing of possible patient parameters and their values as well as a possible output of the evaluation unit 200 according to the invention is presented for the embodiment example shown in FIG. 2.

The known SAPS II value, which is typically used to assess a patient's condition in the intensive care unit, was selected as the evaluation score via the input unit. As a trigger signal, a signal is generated every 60 minutes that triggers the calculations by the evaluation unit 200.

Static patient parameters, received from a patient data management system, are the patient's age and traumatic brain injury diagnosis based on the appropriate ICD 10 code (International Statistical Classification of Diseases and Related Health Problems).

As dynamic readings, values for the following patient parameters are received from external medical devices at regular intervals: Heart rate; systolic blood pressure; body temperature; PaO2/FiO2; export urine. In addition, values for the following patient parameters are available from laboratory results, at least some of which have been automatically transmitted to the evaluation unit: Serum urea; Leukocytes; Serum potassium; Serum sodium; Serum bicarbonate; Serum bilirubin.

The worst values for the patient state are used for the calculation of SAPS II. Therefore, the processing module searches for the worst values for the period Mar. 22, 2021 14:00 to Mar. 23, 2021 14:00 according to the stored calculation rule for SAPS II.

The following values are available in the processing module with the corresponding time stamp after receiving the trigger signal on Mar. 23, 2021 at 14:00:01: Craniocerebral trauma diagnoses: none (Mar. 22, 2021; 14:10:00); age: 55 years (Mar. 22, 2021; 14:10:00); systolic blood pressure: 140 mmHg (Mar. 23, 2021; 13:55:30); heart rate: 125/min (22 Mar. 2021; 16:00:01); Body temperature: 37.2° C. (Mar. 22, 2021; 23:00:05); PaO2/FiO2: 99 mmHg (Mar. 23, 2021; 14:00:01); Urine output: 1 l/d (Mar. 23, 2021; 14:00:00); Serum urea: 0.5 mg/dl (22 Mar. 2021; 15:10:00); leukocytes: 21 (Mar. 22, 2021; 15:10:00); serum potassium: 4.8 (Mar. 22, 2021; 15:10:00); serum sodium: 130 (Mar. 22, 2021; 15:10:00); serum bicarbonate: 14 (Mar. 22, 2021; 15:10:00); serum bilirubin: 66 (Mar. 22, 2021; 15:10:00); GCS: 14 points (recorded by paramedic; Mar. 22, 2021; 13:37:00); TISS 28: 5 points (recorded by nurse; Mar. 22, 2021; 13:45:00).

The representation of the three treatment signals in FIG. 2 is an example. In the exemplary embodiment shown, more or fewer treatment signals can reach the Receiving module at the same time.

Due to the age of the laboratory values, the system calculates a low-priority action recommendation for re-laboratory sampling. In addition, the quality of the laboratory values is only marked as average due to their age and therefore receives a predetermined quality index corresponding to an average quality.

As is well known, the evaluation score according to SAPS II is composed of individual partial scores. In the example discussed, only the following patient parameters contribute to the evaluation score as those with the worst values: Age (7 points); Heart rate (4 points); PaO2/FiO2 (11 points); Leukocytes (3 points), Bicarbonate in serum (6 points); TISS 28 (5 points). This results in an evaluation score of 36 by summation.

The determination of the score of SAPS II is known and is therefore not explained in more detail. The points awarded in each case also result in the corresponding quantitative influence 260 on the evaluation score 134.

The recommended action to check the laboratory values again is already known from the previous processing step. In addition, the system determines that the values used for heart rate and body temperature are already several hours old. For this reason, the calculated quality indicator is reduced according to the stored quality metric for these measurement and laboratory values.

The output provided by the output module via the output signal comprises, in addition to the evaluation score, also the quality indicator, which in this case comprises a discrete classification, preferably a classification into the classes 'Good', 'Average' and 'Poor', whereby in this case, due to the aforementioned non-current laboratory values and the age of the heart rate and body temperature, the classification leads to the result 'Average' for the quality indicator. In the present case, an assignment to the class 'Good' is only made if no additional information, such as the non-current laboratory values, is to be output to the user. An assignment to the class 'Bad', on the other hand, only occurs if such additional information must be output for more than four patient parameters. In addition, the output includes the qualitative influence of the patient parameters on the evaluation score as explained above, preferably a listing of the at least three most influential variables for the evaluation score.

In addition, the output may include a second qualitative influence of the patient parameter quality indices on the quality indicator, preferably a listing of the at least three most influential variables for the quality indicator, presently: serum bicarbonate, heart rate, and serum leukocytes.

Figure 3:
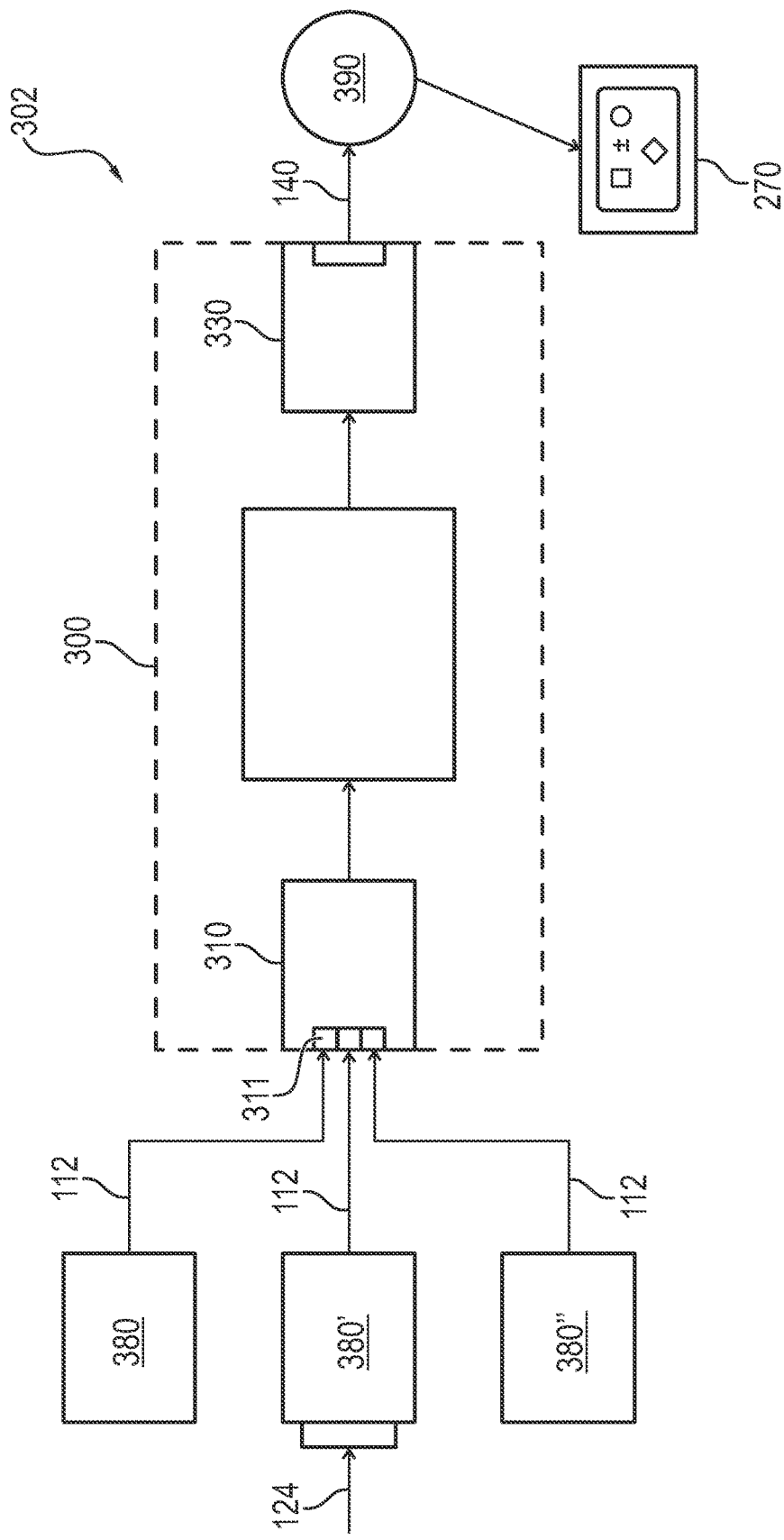
FIG. 3 is a schematic representation of an embodiment of a medical system according to a second aspect of the invention.

FIG. 3 shows a schematic view of an embodiment of a medical system 302 according to a second aspect of the invention.

The medical system 302 includes the evaluation unit 300, which is substantially the same as the evaluation unit 100 of FIG. 1. One difference is that the receiving interface 311 comprises three separate interface portions for receiving at least three different treatment signals 112. The at least three different treatment signals 112 originate from at least three different medical devices 380, 380', 380" connected to the evaluation unit 300. As illustrated, the connection may be made directly via a cable-based and/or wireless connection. Preferably, the communication between medical devices and the evaluation unit is via a network, in particular via a hospital network. One of the medical devices 380' includes a trigger interface 381 through which the trigger signal 124 can be received. The trigger signal is then sent to the Receiving module 310 of the evaluation unit 300 together with the corresponding treatment signal.

The output signal 140 provided by the evaluation unit 300 is again output at the output device 270 of the medical system 302 as an optical output. The output device 270 is connected to the output module 330 via the network 390. The same network is particularly preferably used for communication between the medical devices and the evaluation unit 300.

Preferably, the evaluation unit 300 is also connected to and receives at least one treatment signal from a patient data management system, not shown, via the network, which indicates a value for a patient parameter. The patient data management system preferably outputs static patient parameters, such as age, a treatment duration, and/or a treatment history. Such parameters, which do not change rapidly, can be reliably transmitted to the evaluation unit without the need here for continuous updating of these values for reliable calculation of the evaluation score.

Figure 4:
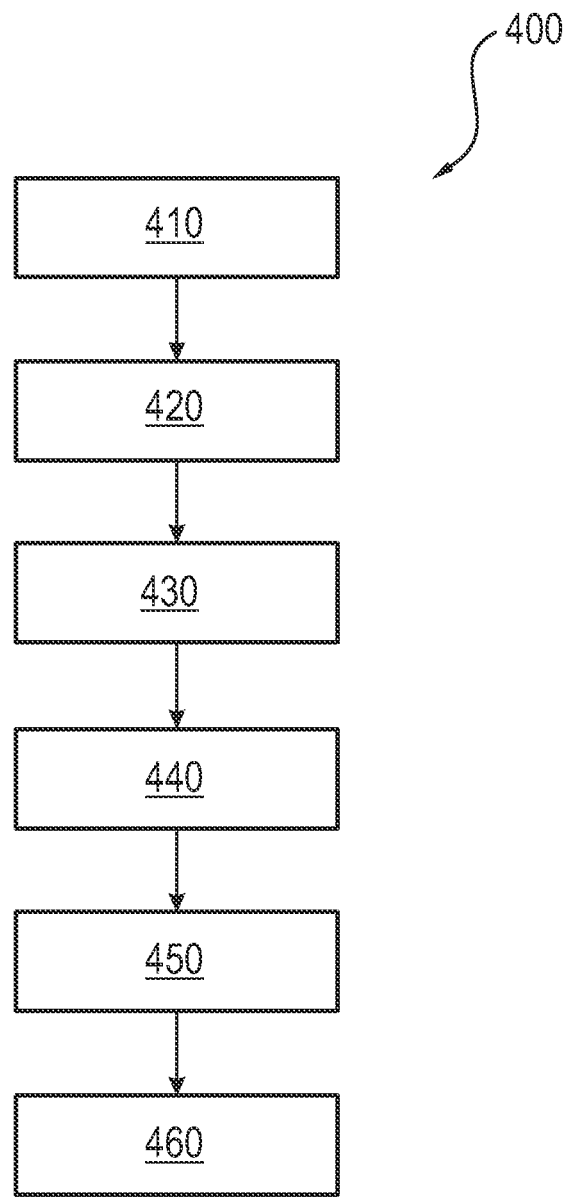
FIG. 4 is a flowchart of an embodiment of a process according to a third aspect of the invention.

FIG. 4 shows a flowchart of an embodiment of a process 400 according to a third aspect of the invention.

The process 400 according to the invention is configured for classifying a current treatment situation. In this context, the process 400 has the steps shown below.

A first step 410 includes receiving a plurality of treatment signals, wherein a respective treatment signal indicates a value for a patient parameter and a signal quality.

A further preferably continuously executed step 420 comprises storing values of patient parameters received at past points in time with a respective time stamp indicating this past point in time and a quality index assigned to the respective value or a group of values, wherein for at least one value or a group of values the quality index is based on the signal quality present at the time of reception.

A next step 430 includes detecting a presence of a trigger signal.

A subsequent step 440 comprises calculating an evaluation score using a stored calculation rule, wherein the calculation is performed using the stored values of patient parameters depending on the respective time stamp, and wherein a lack of a patient parameter necessary for calculating the evaluation score and/or a current value for this patient parameter given the respective time stamp is indicated.

A further step 450 comprises calculating at least one quality indicator based on a stored quality metric depending on the associated quality indices of the values of patient parameters necessary for calculating the evaluation score.

A final step 460 includes providing an output signal, wherein the output signal indicates the evaluation score and the quality indicator.

The process steps of the process 400 according to the invention are preferably executed sequentially, wherein the step 420 to be executed continuously can be executed in parallel with the further process steps. In particular, the step 420 can be continuously executed for several successive processes 400 according to the invention in order to store the received values of patient parameters and the quality index associated with this value or a group of values for further evaluation by calculating the evaluation score.

Preferably, all process steps are executed by a common processor. Alternatively, at least one process step is carried out at a spatial distance from the other process steps, for example by a separate device.

The calculation of the evaluation score according to step 440 and the calculation of the quality indicator according to step 450 typically takes place in near real time. Preferably, a time of less than 20 seconds elapses between the reception of the current treatment signals and the output of the output signal, in particular less than 10 seconds, especially preferably less than 5 seconds. In this case, values for patient parameters older than 20 seconds can also be used. For example, values for patient parameters recorded during the start of the patient's treatment can be used. The past time interval for which received values of a patient parameter are evaluated depends on the patient parameter and is predetermined before the execution of the process. Preferably, these time intervals are stored, for example in the form of time thresholds, together with the corresponding calculation rule and quality metric.

While specific embodiments of the invention have been shown and described in detail to illustrate the application of the principles of the invention, it will be understood that the invention may be embodied otherwise without departing from such principles.

LIST OF REFERENCE CHARACTERS 100, 200, 300 Evaluation unit
105 Housing
110, 210, 310 Receiving module
111, 311 Receive interface
112 Treatment signal
114 Processing signal
115 Patient parameters
116 Value of the patient parameter
120, 220 Processing module
122 Internal memory
123 Trigger receiver component
124 Trigger signal
125 Timestamp
127 Quality (request) index
130, 230, 330 Output (request) module
131 Output interface
132 Calculation rule
134 Evaluation score
136 Quality Metrics
138 Quality indicator
140 Output signal
241 Query interface
245 Inquiry signal
250 Input module
251 User interface
252 User input
260 Quantitative influence
270 Output device
272 optical output
302 medical system
380, 380', 380" medical device
390 Network
400 Procedure
410, 420, 430, 440, 450, 460 Process steps

What is claimed is:

1. An evaluation unit for a signal connected medical system for classifying a current medical treatment situation, the evaluation unit comprising:
   a receiving module configured to receive treatment signals, wherein a respective treatment signal indicates a value for a patient parameter and a signal quality;
   a processing module comprising an internal memory in which values of received patient parameters are stored with a respective time stamp indicating a receipt time and with a quality index assigned to the respective value or a group of values, wherein the quality index is based on a signal quality present at the time of reception, wherein the processing module is configured to:
   detect a presence of a trigger signal;
   with a detection of the trigger signal, to calculate an evaluation score using a stored calculation rule, the calculation being performed using the stored values of patient parameters as a function of the respective timestamp and wherein an absence of a value of a patient parameter necessary for the calculation of the evaluation score is indicated by the evaluation unit or an absence of a current value for the patient parameter based on the respective time stamp is indicated by the evaluation unit or both an absence of a value of a patient parameter necessary for the calculation of the evaluation score and an absence of a current value for the patient parameter based on the respective time stamp is indicated by the evaluation unit; and
   calculate at least one quality indicator based on a stored quality metric depending on the associated quality indices of the values of patient parameters necessary for calculating the evaluation score; and
   an output module configured to provide an output signal that indicates the evaluation score and the quality indicator.

2. An evaluation unit according to claim 1, wherein:
   the processing module is configured to determine a respective quantitative influence of the patient parameters used to calculate the evaluation score and/or on the calculated quality indicator; and
   the output module is further configured to indicate the determined quantitative influence of at least one patient parameter.

3. An evaluation unit according to claim 2, wherein the processing module is adapted to determine the quantitative influence using a sensitivity analysis or an error propagation analysis.

4. An evaluation unit according to claim 2, wherein:
   the output module is further adapted to trigger an output indicating a fault from a predetermined group of faults based on the determined respective quantitative influence of a patient parameter; and
   the predetermined group comprises at least in part: connection failure with a device providing a patient parameter; device failure of a device providing a patient parameter; a new value required for a patient parameter.

5. An evaluation unit according to claim 1, wherein the evaluation unit is configured to receive the trigger signal via the receiving module, or via a user interface, or via a network interface, or via a device interface or via any combination of the trigger signal, the receiving module, the user interface, the network interface, and the device interface.

6. An evaluation unit according to claim 1, wherein the quality indicator is further dependent on the timestamp of a value of a patient parameter necessary for calculating the evaluation score.

7. An evaluation unit according to claim 1, wherein an absence of a value of a patient parameter necessary for the calculation of the evaluation score and/or of a current value for this patient parameter given the respective time stamp is indicated by an output of a request signal to the connected medical system by the evaluation unit.

8. An evaluation unit according to claim 1, wherein:
   the evaluation unit is configured to receive static patient parameters and dynamic patient parameters; and
   the processing module is configured to evaluate only time stamps for values of dynamic patient parameters for the calculation of the evaluation score, whereas values for static patient parameters are evaluated without considering the time stamp.

9. An evaluation unit according to claim 1, wherein the evaluation unit is adapted to receive as static patient parameters age of a patient or gender of a patient or weight of a patient or height of a patient or any combination of age of a patient or gender of a patient or weight of a patient or height of a patient.

10. An evaluation unit according to claim 1, wherein the quality index is based on a time course of a patient parameter and a statistical evaluation of the time course.

11. An evaluation unit according to claim 1, wherein the quality index is based on a time history of signal qualities of treatment signals for a group of received values of a respective patient parameter.

12. An evaluation unit according to claim 1, wherein the calculation of the evaluation score is further based on the respective quality index of used values of the patient parameters.

13. An evaluation unit according to claim 12, wherein the processing module is adapted to consider only values for the calculation of the evaluation score having the quality index in a predetermined index target range.

14. An evaluation unit according to claim 1, wherein the output module is further configured to trigger an alarm in the connected medical system based on the calculated evaluation score and the calculated quality indicator if a predetermined evaluation threshold for the evaluation score is reached and the quality indicator is simultaneously in a quality target range.

15. An evaluation unit in accordance with claim 1, wherein the output signal is configured to be received by a display unit for displaying the evaluation score and the quality indicator.

16. A medical system comprising:
   a plurality of medical devices, wherein the medical devices are configured and adapted to output treatment signals;
   an evaluation unit signal connected to the medical devices for classifying a current medical treatment situation, the evaluation unit comprising:
   a receiving module configured to receive the treatment signals, wherein a respective treatment signal indicates a value for a patient parameter and a signal quality;
   a processing module comprising an internal memory in which values of received patient parameters are stored with a respective time stamp indicating a receipt time and a quality index assigned to the respective value or a group of values, wherein the quality index is based on a signal quality present at the time of reception, wherein the processing module is configured to:

detect a presence of a trigger signal;

with a detection of the trigger signal, to calculate an evaluation score using a stored calculation rule, the calculation being performed using the stored values of patient parameters as a function of the respective timestamp and wherein an absence of a value of a patient parameter necessary for the calculation of the evaluation score is indicated by the evaluation unit or an absence of a current value for the patient parameter based on the respective time stamp is indicated by the evaluation unit or both an absence of a value of a patient parameter necessary for the calculation of the evaluation score and an absence of a current value for the patient parameter based on the respective time stamp is indicated by the evaluation unit; and calculate at least one quality indicator based on a stored quality metric depending on the associated quality indices of the values of patient parameters necessary for calculating the evaluation score; and an output module configured to provide an output signal that indicates the evaluation score and the quality indicator.

17. A medical system according to claim 16, wherein adjusting at least one predetermined treatment parameter of a medical device of the plurality of medical devices triggers the trigger signal for the evaluation unit.

18. A medical system in accordance with claim 16, further comprising:

a display unit, the display unit being configured to receive the output signal, the display unit being configured to display the evaluation score and the quality indicator based on the output signal.

19. A process for classifying a current medical treatment situation, the process comprising the steps of:

receiving a plurality of treatment signals, wherein a respective treatment signal indicates a value for a patient parameter and a signal quality;

storing values of patient parameters received at past times with a respective time stamp indicating the past time and a quality index assigned to the respective value or a group of values, wherein for at least one value or a group of values the quality index is based on the signal quality present at the time of reception;

detecting a presence of a trigger signal;

calculating an evaluation score using a stored calculation rule, the calculation being performed using the stored values of patient parameters as a function of the respective time stamp, and indicating an absence of a patient parameter necessary for calculating the evaluation score or indicating an absence of a current value for the patient parameter in view of the respective time stamp or indicating both an absence of a patient parameter necessary for calculating the evaluation score and an absence of a current value for the patient parameter in view of the respective time stamp;

calculating at least one quality indicator based on a stored quality metric depending on the associated quality indices of the values of patient parameters necessary for calculating the evaluation score;

providing an output signal, wherein the output signal indicates the evaluation score and the quality indicator.

20. A process in accordance with claim 19, further comprising:

providing a display unit;

transmitting the output signal to the display unit;

displaying the evaluation score and the quality indicator on the display unit.

* * * * *